(12) United States Patent
Birnholz et al.

(10) Patent No.: US 6,365,200 B1
(45) Date of Patent: Apr. 2, 2002

(54) TOPICAL SKIN SENSITIZER

(76) Inventors: Jason C. Birnholz; Frances B. Kent, both of The E-Gal Corp., 600 Central Ave., Highland Park, IL (US) 60035

( * ) Notice: Subject to any disclaimer, the term of this patent is extended or adjusted under 35 U.S.C. 154(b) by 0 days.

(21) Appl. No.: 09/619,913

(22) Filed: Jul. 19, 2000

(51) Int. Cl.⁷ .................. A01N 65/00; A61K 35/78; A61K 39/385
(52) U.S. Cl. .................. 424/744; 424/728; 424/725
(58) Field of Search .................. 514/54, 53; 510/406, 510/437, 428, 427, 138; 424/725, 744, 728

(56) References Cited

U.S. PATENT DOCUMENTS 6,080,707 A * 6/2000 Glenn, Jr. et al. .......... 510/130
6,083,932 A * 7/2000 Pang et al. .................. 514/54

* cited by examiner

*Primary Examiner*—Jon P. Weber
*Assistant Examiner*—Patricia Patton
(74) *Attorney, Agent, or Firm*—Charles E. Temko

(57) ABSTRACT

A topically applied aphrodisiac dispersed in a manually applied vehicle which substantially increases tissue sensation. The active ingredients are benzalkonium chloride, aloe and vitamin E in a water soluble gel which includes sorbitol, glycerin, and hydroxethylcellulose.

6 Claims, No Drawings

TOPICAL SKIN SENSITIZER

BACKGROUND OF THE INVENTION

This invention relates generally to the field of chemical aphrodisiacs, and more particularly to a topical medicament which is applied to sensitive tissue areas to produce increased sensitivity to physical contact.

Internally taken aphrodisiacs are well-known in the art as is the resultant psychological effect of using the same. The use of such preparations, in many cases, is accompanied by some disadvantages, including time delay before taking effect, various side effects resulting from ingestion, and often, the lack of useful effect.

The use of benzalkonium chloride as a virucidal agent in the treatment of AIDS and related disease is known, as is the use of this compound as a spermicidal agent when incorporated into a suppository. It is also known to use this composition in aqueous, Quaternary ammonium antiseptics, and disinfectants.

In the composition described in our prior U.S. Pat. Nos. 5,902,593 and 5,976,561, a small amount of propylene glycol is employed as a gel thickener, which has now been found to be unnecessary. As a preservative, use is made of methylchloroisothiazolinone and methylisothiazoline, both of which have tended to cause irritation during use, as well as affect the complete clarity of the gel.

The improved composition disclosed herein has eliminated these components. The use of dmdm hydantoin has provided substantial decrease in the irritation rate of the original composition without affecting its primary effect as a topical aphrodisiac. We have also provided additives to improve texture of the composition to retard evaporative drying and effect healing of irritated tissues.

SUMMARY OF THE INVENTION

Briefly stated, the invention contemplates the use of benzalkonium chloride as a skin and tissue sensitizer, particularly effective when manually applied in a gel vehicle to vaginal areas, wherein the thinly spread gel also serves as an effective lubricant. The product may be applied immediately before intercourse, and will remain effective for a substantial period of time thereafter.

As contrasted with our earlier composition, we have provided an improved preservative in the form of dmdm hydantoin to result in decreased tissue irritation without any adverse effect. In addition, we have incorporated additional ingredients which improve the texture and surface spreading of the composition, namely aloe and vitamin E, which stabilizes the ionic environment of nerve endings in the skin and facilitates their re-polarization.

DETAILED DESCRIPTION OF THE DISCLOSED EMBODIMENT

In accordance with the invention, the disclosed embodiment is in the form of a water soluble gel. As in our prior composition, the principal effective ingredient is benzalkonium chloride in a spreadable vehicle, which may include other known ingredients to provide desirable characteristics in terms of odor, spreadability, adherence to the applied area, and chemical stability. A suitable gel includes water, glycerin, hydroxyethylcellulose, aloe barbadensis gel and/or vitamin E. These ingredients improve the texture and surface spreading of the composition in a noticeable way. Aloe is well known in the art for its anti-inflammatory and wound healing properties, and is a component in a cosmetic skin cleaner described in the Menzel, et al., U.S. Pat. No. 5,993,857. Recent works have also suggested that substances can be purified from aloe with anti-oxidant and antiviral properties, as disclosed in the patent to Yu, et al., U.S. Pat. No. 5,939,395. The Shand, et al., U.S. Pat. No. 5,902,796, discloses certain bioactive factors of aloe vera plants. The formulation may include cyclomethicone, dimethicone, dimethicone copolyol or related substances in order to retard lost lubricity with drying of the gel.

The subject of ion channels in the function of sensory nerves is reviewed by the Hahn U.S. Pat. No. 5,958,436, and is pertinent to the effect of benzalkonium chloride in the present preparation. We have selected the anti-oxidant vitamin E for stabilizing the ionic environment of the nerve endings in the skin, and facilitating their re-polarization.

The present composition has been tested using high resolution ultrasound imaging and one and two dimensional Doppler ultrasound techniques and impedance plethysmographY ("Registran") to study arousal in both men and women before and after application of the composition. As impressive as blood flow changes and local firmness of the penis and clitoris are with use in a laboratory setting, we are aware that they do not represent the subjective and satisfaction components of sexual activity in privacy. To this end, we have continued to rely upon questionnaires, diaries, and comments of users.

We have begun to use the composition as a coupling agent for ultrasound scanning, in particular endovaginal and endorectal studies and for volume image reconstruction (3D ultrasound). The lubricant facilitates probe (transducer) placement and scanning motion, the anti-microbial properties of the present formulation decrease interpersonal disease transmission, and the anti-inflammatory properties of the aloe decrease the possibility of post-scan irritation. The following examples are illustrative. Parts are by weight.

EXAMPLE 1

|  | % Range by Weight |
| --- | --- |
| Water | 70–80 |
| Hydroxyethylcellulose | 1–2 |
| Sorbitol | 5–10 |
| Glycerin | 5–10 |
| Benzalkonium chloride | 0.50 |
| DMDM Hydantoin | 0.30–0.50 |
| Ginseng Extract | 0.10–0.30 |
| Citric Acid | 0.01–0.10 |
| Fragrance | 0.05–0.20 |
| Aloe Barbadensis Gel | 10–15 |

EXAMPLE 2

|  | % Range by Weight |
| --- | --- |
| Water | 70–80 |
| Hydroxyethylcellulose | 1–2 |
| Sorbitol | 5–10 |
| Glycerin | 5–10 |
| Benzalkonium chloride | 0.50 |
| DMDM Hydantoin | 0.30–0.50 |
| Ginseng Extract | 0.10–0.30 |
| Citric Acid | 0.01–0.20 |
| Fragrance | 0.05–0.10 |
| Aloe Barbadensis Gel | 10–15 |
| Tocopherol Acetate | 0.01–0.10 |

EXAMPLE 3

|  | % Range by Weight |
|---|---|
| Water | 70–80 |
| Hydroxyethylcellulose | 1–2 |
| Sorbitol | 5–10 |
| Glycerin | 5–10 |
| Benzalkonium chloride | 0.50 |
| DMDM Hydantoin | 0.30–0.50 |
| Ginseng Extract | 0.10–0.30 |
| Citric Acid | 0.01–0.20 |
| Fragrance | 0.05–0.10 |
| Aloe Barbadensis Gel | 10–15 |
| Tocopherol Acetate | 0.01–0.10 |
| Copolyol dimethicone | 0.5–20.0 |

The gel forming components are preferably first mixed in a suitable mixing device, including the aloe barbadensis and vitamin E, the former being commercially available as a gel, following which the benzalkonium chloride is added. Operations may be conducted at room temperature. The resultant product is preferably packaged in a flexible tube suitable for dispensing upon the fingers of a user or direct application.

While it is difficult to quantify the degree of increased sensitivity obtained, the product has been tested, by individuals who applied a light coating of the gel to appropriate areas immediately before intercourse. Without exception, each of the users reported increased pleasure during intercourse to a substantial degree when compared to intercourse without using the product due to increased skin sensitivity. In some cases, the product was applied by coating the outer surface of a condom. The effect was observed to extend over a substantial period of time after application particularly with the silicone enabled preparations. In the case of new users, no skin irritation has occurred, and in the case of users of our earlier composition, use of the new composition assists in healing irritation already present. It is to be noted that all of the ingredients in the product have been approved for medical use by the Federal Food & Drug Administration.

We wish it to be understood that we do not consider the invention to be limited to the precise details set forth in the specification, for obvious modifications will occur to those skilled in the art to which the invention pertains.

We claim:

1. A topical skin sensitizer comprising a water soluble gel vehicle and active ingredients consisting of benzalkonium chloride, vitamin E, and aloe.

2. A topical skin sensitizer in accordance with claim 1, in which said vehicle comprises water, sorbitol, glycerin, and hydroxyethylcellulose.

3. A topical skin sensitizer in accordance with claim 1, in which said vehicle comprises water, sorbitol, glycerin, hydroxyethylcellulose and dimethicone.

4. A topical skin sensitizer consisting of the following formulation:

|  | % Range by Weight |
|---|---|
| Water | 70–80 |
| Hydroxyethylcellulose | 1–2 |
| Sorbitol | 5–10 |
| Glycerin | 5–10 |
| Benzalkonium chloride | 0.50 |
| DMDM Hydantoin | 0.30–0.50 |
| Ginseng Extract | 0.10–0.30 |
| Citric Acid | 0.01–0.10 |
| Fragrance | 0.05–0.20 |
| Aloe Barbadensis Gel | 10–15. |

5. A topical skin sensitizer consisting of the following formulation:

|  | % Range by Weight |
|---|---|
| Water | 70–80 |
| Hydroxyethylcellulose | 1–2 |
| Sorbitol | 5–10 |
| Glycerin | 5–10 |
| Benzalkonium chloride | 0.50 |
| DMDM Hydantoin | 0.30–0.50 |
| Ginseng Extract | 0.10–0.30 |
| Citric Acid | 0.01–0.20 |
| Fragrance | 0.05–0.10 |
| Aloe Barbadensis Gel | 10–15 |
| Tocopherol Acetate | 0.01–0.10. |

6. A topical skin sensitizer consisting of the following formulation:

|  | % Range by Weight |
|---|---|
| Water | 70–80 |
| Hydroxyethylcellulose | 1–2 |
| Sorbitol | 5–10 |
| Glycerin | 5–10 |
| Benzalkonium chloride | 0.50 |
| DMDM Hydantoin | 0.30–0.50 |
| Ginseng Extract | 0.10–0.30 |
| Citric Acid | 0.01–0.20 |
| Fragrance | 0.05–0.10 |
| Aloe Barbadensis Gel | 10–15 |
| Tocopherol Acetate | 0.01–0.10 |
| Copolyol dimethicone | .5–20.0. |

* * * * *